(12) United States Patent
Alpern et al.

(10) Patent No.: US 6,719,128 B2
(45) Date of Patent: Apr. 13, 2004

(54) PILLOW-SHAPED SUTURE PACKAGE WITH PRESSURE PANEL

(75) Inventors: Marvin Alpern, Glen Ridge, NJ (US); Delfin A. Lorenzo Iglesias, San Juan, PR (US)

(73) Assignee: Ethicon, Inc., Somerville, NJ (US)

( * ) Notice: Subject to any disclaimer, the term of this patent is extended or adjusted under 35 U.S.C. 154(b) by 123 days.

(21) Appl. No.: 09/925,240

(22) Filed: Aug. 9, 2001

(65) Prior Publication Data

US 2003/0029737 A1 Feb. 13, 2003

(51) Int. Cl.[7] .................. A61B 17/06; B65D 85/28; B65D 85/00
(52) U.S. Cl. ............ 206/63.3; 206/380; 206/388; 606/228
(58) Field of Search ............... 206/63.3, 380, 206/388, 49; 229/128, 155, 906, 76, 84; 242/170, 174; 606/228; 132/323

(56) References Cited

U.S. PATENT DOCUMENTS

| | | | | |
|---|---|---|---|---|
| 2,108,451 A | * | 2/1938 | Selezneff | 229/84 |
| 2,964,227 A | * | 12/1960 | Goldsholl | 229/128 |
| 3,010,571 A | * | 11/1961 | Transport | 229/128 |
| 3,126,145 A | * | 3/1964 | Struble | 229/128 |
| 4,572,363 A | * | 2/1986 | Alpern | 206/63.3 |
| 4,884,681 A | | 12/1989 | Roshdy et al. | |
| 4,887,710 A | | 12/1989 | Roshdy et al. | |
| 4,946,043 A | | 8/1990 | Roshdy et al. | |
| 5,284,240 A | | 2/1994 | Alpern et al. | |
| 5,494,154 A | * | 2/1996 | Ainsworth et al. | 206/63.3 |
| 5,555,976 A | * | 9/1996 | Pernot | 206/63.3 |
| 5,788,063 A | * | 8/1998 | Van Ness | 206/63.3 |
| 5,911,358 A | * | 6/1999 | Kenner et al. | 229/128 |
| 5,979,745 A | * | 11/1999 | Surlina | 229/128 |
| 6,029,805 A | * | 2/2000 | Alpern et al. | 206/63.3 |
| 6,045,035 A | * | 4/2000 | Murakami et al. | 206/63.3 |

* cited by examiner

Primary Examiner—Mickey Yu
Assistant Examiner—Gregory Pickett

(57) ABSTRACT

A suture package is disclosed that is sized and shaped to contain at least one suture. The suture package includes an envelope having a plurality of panels. One of the panels is a pressure panel which functions to urge a suture against another of the panels, thereby immobilizing the suture within the package.

17 Claims, 4 Drawing Sheets

PILLOW-SHAPED SUTURE PACKAGE WITH PRESSURE PANEL

FIELD OF THE INVENTION

The present invention relates to a suture package, and more specifically to a suture package that immobilizes sutures contained therein.

BACKGROUND OF THE INVENTION

Sutures are typically packaged in individual packages containing one or more sutures. Conventionally, sutures are packaged in a heavy foil wrapped around a coil of the suture. The package is then sealed into a tear-open foil primary package; and, thereafter, the primary package is over wrapped in a sealed plastic pouch. Unfortunately, the heavy foil, which is wrapped around the sutures, occasionally punctures the tear-open foil primary package.

An alternative approach includes packaging sutures in a flat, paper folder in lieu of a heavy foil to retain the sutures. When such a folder contains sutures, which are of large, gauge or long length or which comprise a large number of strands, the folder often bulges undesirably and becomes distorted. In turn, the distortion causes the folder to strain; and, as a result, it may be difficult to close the folder during assembly or to open the folder during a surgical procedure.

Yet another approach includes packaging sutures in a package with a greater internal volumetric capacity relative to the flat, paper folder. These high volume packages may accommodate large gauge sutures without the problems associated with the flat, paper folder. However, when thinner or shorter sutures or sutures with a small number of strands are stored therein, the sutures may move around in the package and may become tangled.

Accordingly, there is a need for a novel suture package that immobilizes sutures therein, and that otherwise overcomes the disadvantages of the prior art discussed above.

SUMMARY OF THE INVENTION

A suture package is disclosed that is sized and shaped to contain at least one suture. The suture package includes an envelope having a first panel and a second panel, which cooperate to form an interior hollow. A third panel is also included which extends within the envelope such that it is biased toward the second panel, whereby a suture contained within the hollow is urged against the second panel by the third panel.

A method is also disclosed for assembling a suture package from a blank. Initially, the blank is provided with a plurality of holes. The blank is placed onto a winding apparatus having a pair of pins such that the pins pass through the holes in the blank. The third panel is then folded against the first panel such that a free end of the third panel extends to the fold line.

A suture is wound around the pins; and, thereafter, the blank and the suture are removed from the winding apparatus as a unit. The first panel and the second panel are folded toward each other. Lastly, a pillow-shaped envelope is formed in which the second and third panels assume generally matching arcuate shapes with the suture being urged against the second panel by the third panel.

Other features and aspects of the present invention will become more fully apparent from the following detailed description of the preferred embodiments, the appended claims and the accompanying drawings.

BRIEF DESCRIPTION OF THE DRAWINGS

For a more complete understanding of the present invention, reference is made to the following detailed description of various exemplary embodiments considered in conjunction with the accompanying drawings, in which.

DETAILED DESCRIPTION OF THE PREFERRED EMBODIMENTS

Figure 1:
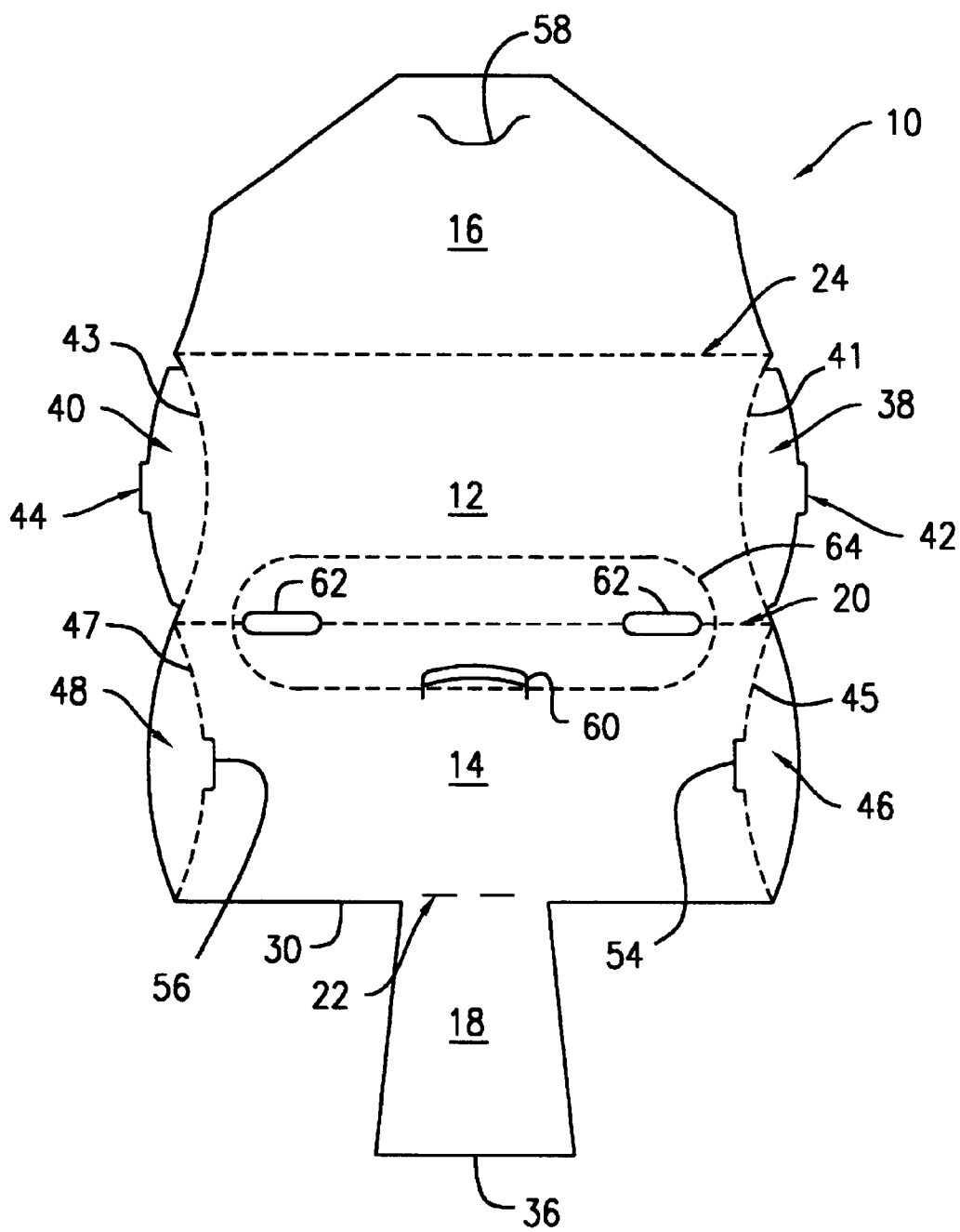
FIG. 1 is a plan view of a blank used to produce a suture package in accordance with an exemplary embodiment of the present invention.

FIG. 1 shows a suture package 10 in an unfolded state, i.e., as a flat blank used to produce a suture package 10 in accordance with the present invention. The suture package 10 includes a center panel 12, a back panel 14, a cover panel 16, and a pressure panel 18. It will be understood that the cover panel 16 is an optional feature.

The back panel 14 is connected to the center panel 12 at a first fold line 20 along one edge of the back panel 14, and to the pressure panel 18 at a second fold line 22 along an opposite edge of the back panel 14. The cover panel 16 is connected to the center panel 12 at a third fold line 24 along an edge of the center panel 12 which is distal to the first fold line 20. The second fold line 22 preferably has relatively few perforations so as not to excessively diminish the resilience of the pressure panel 18 that tends to bias it toward its unfolded position.

In embodiments, which do not employ the cover panel 16, the third fold line 24 would be the distal edge of the center panel 12 relative to the first fold line 20. In all embodiments, the back panel 14 also has a distal edge 30 relative to the first fold line 20.

The pressure panel 18 has a free end 36 distal to the second fold line 22. The pressure panel 18 has a length measured from the second fold line 22 to the free end 36 such that the free end 36 is sized and shaped to extend to the first fold line 20 when the pressure panel 18 is folded flat against the back panel 14.

An end panel 38 is attached to one end of the center panel 12 along a fold line 41, and an end panel 40 is attached to an opposite end of the center panel 12 along a fold line 43. The end panels 38, 40 have a double convex shape such that when the suture package 10 is folded and assembled, the end panels 38, 40 are substantially perpendicular to the center panel 12 and function as side panels for the resulting envelope-like package. An outer tab 42 extends outwardly from the end panel 38, and likewise an outer tab 44 extends outwardly from the end panel 40.

The suture package 10 further includes two additional end panels 46, 48, each having a double convex shape. The end panel 46 is attached to one end of the back panel 14 along a fold line 45, and the end panel 48 is attached to one end of the back panel 14 along a fold line 47. When the end panels 38, 40, 46, 48 are folded about their respective fold lines 41, 43, 45, 47, the end panels 46, 48 are substantially perpendicular to the back panel 14, and overlap the end panels 38, 40 of the center panel 12. However, when folded, the end panels 46, 48 do bend slightly to form a concave surface S (see FIG. 2) relative to the fold lines 41, 43, 45, 47, which may be either perforated, creased, etc.

The fold line 45 includes a first slit 54, and the fold line 47 includes a second slit 56. When the end panels 46, 48 are folded about their respective fold lines 45, 47, the first slit 54 forms a first slot 54' (see FIG. 2) and an inner tab 50 (see FIG. 2) on the end panel 46, while the second slit 56 forms a second slot 56' (see FIG. 2) and an inner tab 52 (see FIG. 2) on the end panel 48. The inner tabs 50, 52 extend inwardly relative to the back panel 14. The slots 54', 56' are sized and shaped to receive the outer tabs 42, 44, respectively, of the end panels, 38, 40, when the suture package 10 is assembled.

The cover panel 16 has a third slit 58 that forms a locking tab 58' (see FIG. 3) sized and shaped to be received in a slot 60 that is cut in the back panel 14 so as to retain the cover panel 16 in a position overlying the back panel 14 when the suture package 10 is assembled.

A plurality of holes 62 is provided proximate the first fold line 20. The holes 62 are sized and shaped to allow pins from a suture winding apparatus (not shown) to pass therethrough.

Figure 2:
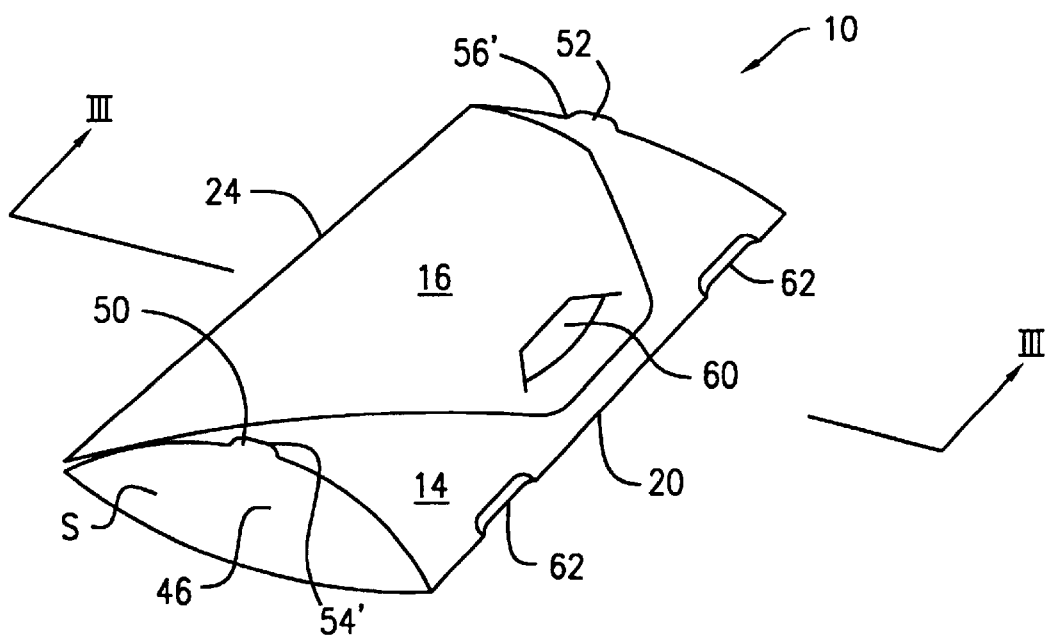
FIG. 2 is a perspective view of a suture package made from the blank shown in FIG. 1.

An assembled/folded suture package 10 is shown in FIG. 2, which illustrates the relative position of the various components of the suture package 10. The suture package 10 shown in FIG. 2 is made from the blank shown in FIG. 1.

The following description will describe the loading and folding of a suture package 10, i.e., to make the conversion from the configuration shown in FIG. 1 to that shown in FIG. 2. Initially, the flat suture package 10 is placed onto a suture winding apparatus (not shown) having a pair of pins, with the pins extending through the holes 62. The pressure panel 18 is then folded flat against the back panel 14 along the second fold line 22 such that the free end 36 extends to the first fold line 20. At least one suture 64 (see FIG. 3) is wound around the pins in a conventional manner.

The suture package 10 and the suture 64 overlaid thereover are then removed from the suture winding apparatus, i.e., the suture package 10 is lifted off the winding pins to thereby simultaneously pull the suture 64 from its position looped around the winding pins. The suture 64 offers some resistance to being withdrawn from the pins of the suture winding apparatus, tending to fold the suture package 10 at the first fold line 20. The operator will typically manually retain the suture 64 (shown diagrammatically in dotted lines in FIG. 1) in proper position relative to the suture package 10 as it is withdrawn from the suture winding apparatus.

The center panel 12 and the back panel 14 are then folded toward each other so as to form an envelope having an interior hollow to contain the suture 64 within the hollow and such that the distal edge (shown by the third fold line 24) of the center panel 12 is positioned adjacent to and abutting the distal edge 30 of the back panel 14. If the cover panel 16 is not employed, the distal edge (shown by the third fold line 24) is secured to the distal edge 30 by a conventional attaching means, such as adhesive, heat, seal, etc.

The cover panel 16 is then folded over the back panel 14 and secured into position by inserting the locking tab 58' of the cover panel 16 into the slot 60 of the back panel 14 and closing the suture package 10. It will be understood that other means to secure the cover panel 16 in a position overlying the back panel 14 may be employed, such as adhesive, etc.

The distal edge (the third fold line 24) of the center panel 12 and the distal edge 30 of the back panel 14 are pushed slightly toward the first fold line 20 so as to bend the panels 12, 14, 16, which creates a generally three-dimensional pillow shape for the envelope. In turn, the contact between the free end 36 of the pressure panel 18 and the first fold line 20 causes the pressure panel 18 to resiliently bend in a generally matching arcuate shape as the center panel 12.

Figure 3:
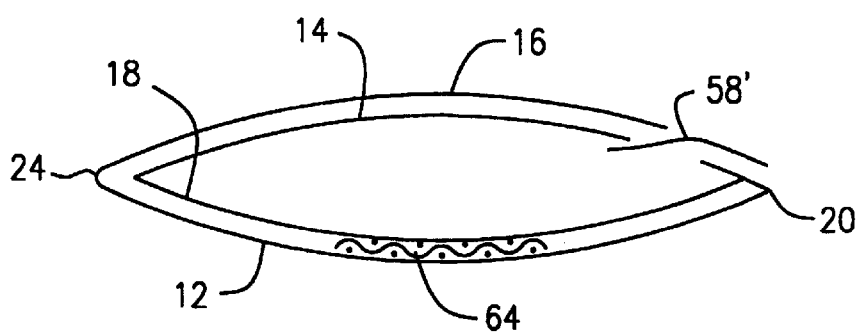
FIG. 3 is a cross-sectional view of the suture package of FIG. 2, taken along line III—III and looking in the direction of the arrows.

In this position, the pressure panel 18 will apply pressure to the suture 64, which is captured between the pressure panel 18 and the center panel 12 as illustrated in FIG. 3, which shows the relative position of the panels 12, 14, 16, 18, and the suture 64. Also in this position, the pressure panel 18 is extended within the envelope such that the pressure panel 18 is biased toward the center panel 12, whereby the suture 64 is urged against the center panel 12 by the pressure panel 18.

The end panels 38, 40, 46, 48 are folded inwardly about their respective fold lines 41, 43, 45, 47 such that the end panels 46, 48 of the back panel 14 overlap the end panels 38, 40 of the center panel 12 so as to maintain the three-dimensional pillow shape of the envelope. Final assembly of the suture package 10 is performed by engaging the outer tabs 42, 44 of the end panels 38, 40 with the slots 54', 56' so as to lock the end panels 38, 40, 46, 48 in position.

Because the pressure panel 18 in the suture package 10 exhibits some degree of flexibility, it functions to immobilize sutures of various different gauges, lengths, and quantities within the suture package 10, without the use of heavy foil. The pressure panel 18 also functions to prevent tangling and clumping of a variety of sutures that may be contained in the suture package 10.

Placing the suture package 10 on the suture winding apparatus behind the suture 64 simplifies the packaging process and reduces the time that would be needed to insert a separately wound suture coil into a preassembled cardboard container. The use of the suture package 10 is conveniently integrated with the suture winding process and therefore does not significantly increase assembly time over that encountered with conventional forms of suture packaging. The suture package 10 is also easily opened to facilitate dispensing of sutures.

Figure 4:
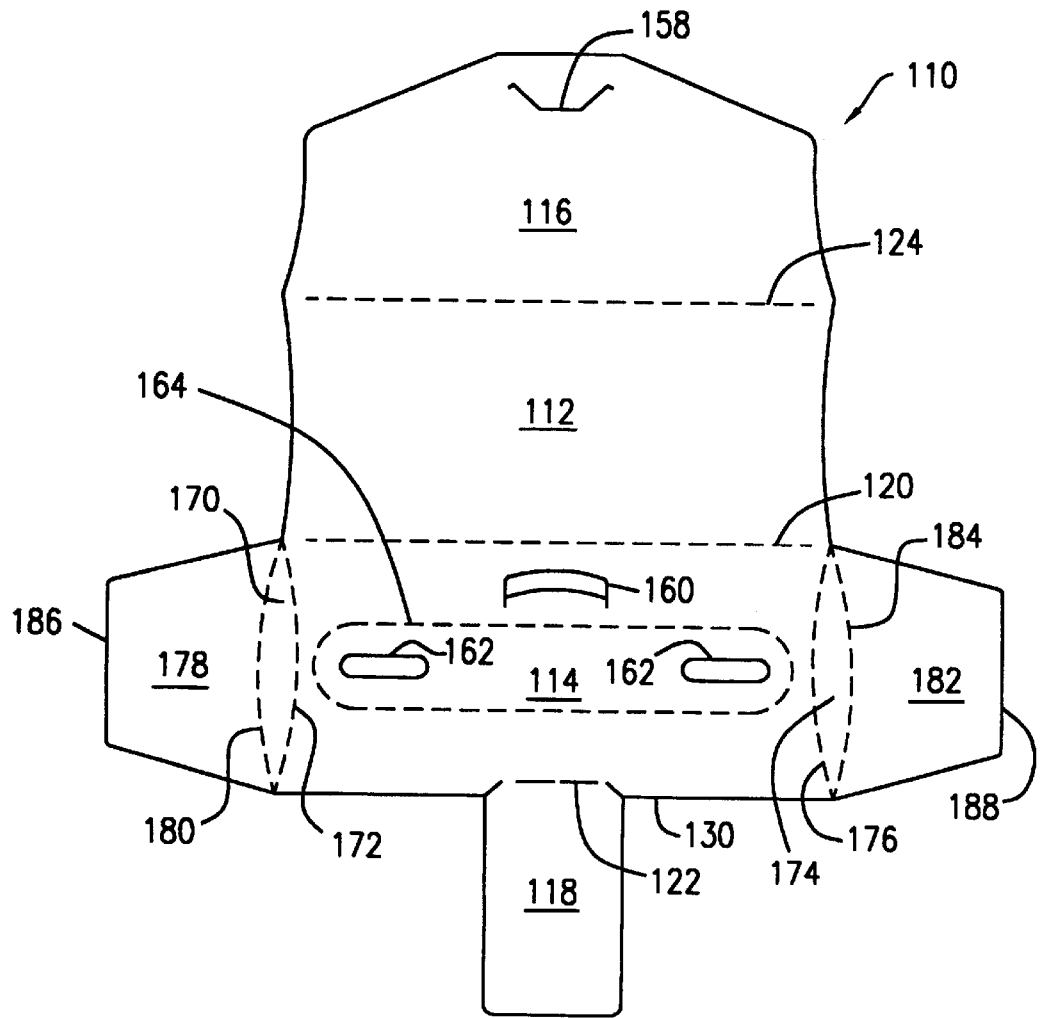
FIG. 4 is a plan view of a blank used to produce a suture package in accordance with another exemplary embodiment of the present invention.
Figure 5:
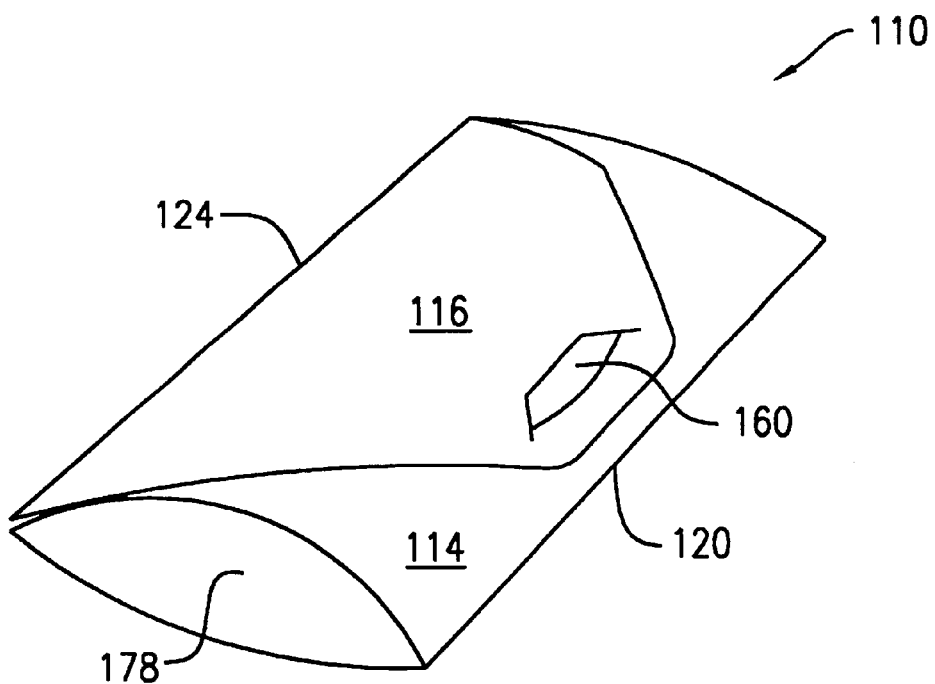
FIG. 5 is a perspective view of a suture package made from the blank shown in FIG. 4.

Another exemplary embodiment of the present invention is illustrated in FIGS. 4 and 5. Elements illustrated in FIGS. 4 and 5 which correspond to the elements described above with reference to FIGS. 1–3 have been designated by corresponding reference numerals increased by one hundred. The embodiment of FIGS. 4 and 5 operates in the same manner and provides the same basic advantages as the embodiment of FIGS. 1–3, unless it is otherwise stated.

FIG. 4 shows a suture package 110 in an unfolded state, i.e., as a flat blank used to produce a suture package 110 in accordance with the present invention. The suture package 110 includes a center panel 112, a back panel 114, a cover panel 116, and a pressure panel 118. The suture package 110 includes an end panel 170 attached to one end of the back panel 114 along a fold line 172, and an end panel 174 attached to an opposite end of the back panel 114 along a fold line 176. Like the end panels 38, 40, 46, 48 (see FIG. 1), the end panels 170, 174 also have a double convex shape.

A flap 178 is attached to the end panel 170 along a fold line 180 and a flap 182 is attached to the end panel 174 along a fold line 184. The fold lines 172, 176, 180, 184 may be either perforated, creased, etc. The flap 178 has a free end 186 distal to the fold line 180 and likewise, the flap 182 has a free end 188 distal to the fold line 184.

The flaps 178, 182 have a length measured from their respective fold lines 180, 184 such that the free ends 186, 188 are sized and shaped to extend to an area on the back panel 114 between their respective end panels 170, 174 and a slot 160 when the flaps 178, 182 are folded against the back panel 114. When the flaps 178, 182 are folded about their respective fold lines 180, 184, the end panels 170, 174 fold along their respective fold lines 172, 176 such that the end panels 170, 174 are substantially perpendicular to the back panel 114 and function as side panels for the resulting envelope-like package.

The back panel 114 of the suture package 110 also includes holes 162 which are located intermediate a fold line 120 and a distal edge 130 relative to said first fold line 120. This is unlike the suture package 10 shown in FIG. 1, wherein the holes 62 are located proximate the first fold line 20.

The following description will describe the loading and folding of the suture package 110, i.e., to make the conversion from the configuration shown in FIG. 4 to that shown in FIG. 5. Initially, the flat suture package 110 is placed onto a suture winding apparatus (not shown) having a pair of pins, with the pins extending through the holes 162. The pressure panel 118 is then folded flat against the back panel 114 along a second fold line 122 such that a free end 136 of the pressure panel 118 extends to the first fold line 120. At least one suture 164 is wound around the pins in a conventional manner.

The flaps 178, 182 are then folded against the back panel 114 along their respective fold lines 180, 184 such that the end panels 170, 174 fold along their respective fold lines 172, 176 to form side panels for the resulting envelope-like package. As the end panels 170, 174 fold, the back panel 114 bends into a bow-shaped configuration.

The center panel 112 and the back panel 114 are then folded toward each other so as to form an envelope having an interior hollow to contain the suture 164 within the hollow and such that the distal edge (indicated by a third fold line 124) of the center panel 112 is positioned adjacent to and abutting the distal edge 130 of the back panel 114. If the cover panel 116 is not employed, final assembly is performed by securing the distal edge (indicated by the third fold line 124) to the distal edge 130 by a conventional attaching means, such as adhesive, heat, seal, etc.

In this position, the center panel 112 bends into a bowed-shaped configuration, whereby the center panel 112 cooperates with the back panel 114 to create a generally three-dimensional pillow shape for the envelope. The contact between the free end 136 of the pressure panel 118 and the first fold line 120 causes the pressure panel 118 to resiliently bend in a generally matching arcuate shape as the center panel 112.

Final assembly of the suture package 110 is performed by folding the cover panel 116 over the back panel 114 and securing the cover panel 116 into position by inserting the locking tab (not shown) of the cover panel 116 into the slot 160 of the back panel 114 and closing the suture package 110. It will be understood that other means to secure the cover panel 116 in a position overlying the back panel 114 may be employed, such as adhesive, etc.

Figure 6:
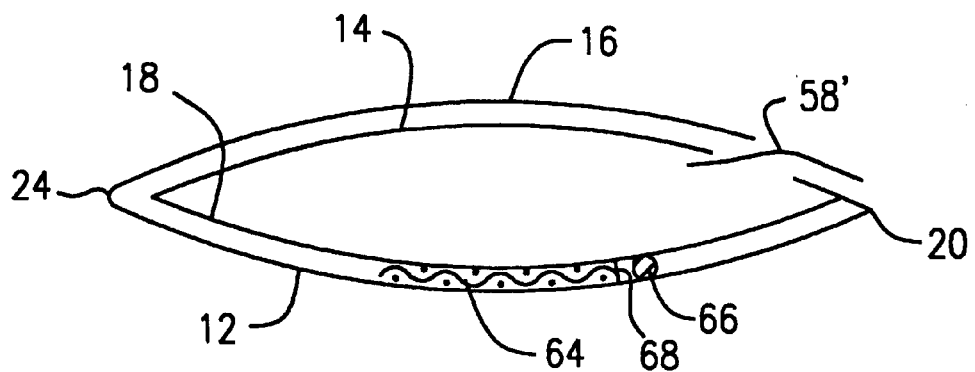
FIG. 6 is a view similar to the view of FIG. 3, except that the suture is shown with a needle attached thereto.

The foregoing description discloses only the preferred embodiments of the invention. Modifications of the above-disclosed apparatus that fall within the scope of the invention will be readily apparent to those of ordinary skill in the art. For example, it should be noted that although FIG. 1, FIG. 3, and FIG. 4 illustrate only a single suture 64, 164, more than one suture may be contained within the suture package 10, 110. In a further modification, the suture package 10, 110 can also be used for armed sutures, i.e., a suture with a needle 66 (see FIG. 6) attached thereto. With reference to FIG. 6, the suture package 10 employs a paper board 68 to separate the suture 64 from the needle 66, thereby preventing the needle 66 from damaging the suture 64. Moreover, the suture package 10 can use alternative adhesive attaching means to lock the end panels 38, 40, 46, 48 in place. In yet another modification, the end panels 38, 40 can be provided with the inner tabs 50, 52, while the end panels 46, 48 can be provided with the outer tabs 42, 44. Accordingly, while the present invention has been disclosed in connection with the preferred embodiments thereof, it should be understood that other embodiments may fall within the spirit and scope of the invention, as defined by the following claims.

The invention claimed is:

1. A suture package comprising an envelope having a first panel and a second panel which cooperate to form an interior hollow, said first panel bulging outwardly in a first direction so as to assume a first arcuate shape, said second panel bulging outwardly in a second direction substantially opposite to said first direction so as to assume a second arcuate shape; a third panel extending within said envelope and having a width which is substantially smaller than the width of said first panel; and a suture positioned within said interior hollow between said second panel and said third panel, said third panel bulging outwardly in said second direction such that said third panel assumes a third arcuate shape which substantially matches said second arcuate shape of said second panel and such that said third panel is biased toward said second panel so as to urge said suture against said second panel.

2. The suture package of claim 1, wherein said second panel is connected to said first panel at a first fold line along one side of said first panel; and said third panel is connected to said first panel at a second fold line along an opposite side of said first panel, said first panel and said second panel being foldable relative to each other along said first fold line to form said envelope.

3. The suture package of claim 2, wherein said first panel and said second panel are substantially coextensive.

4. The suture package of claim 3, further comprising attaching means for attaching said opposite side of said first panel to a distal side of said second panel opposite said first fold line.

5. The suture package of claim 4, wherein said envelope is generally pillow-shaped.

6. The suture package of claim 5, wherein said third panel includes a free end which abuts said first fold line after said third panel is folded about said second fold line.

7. The suture package of claim 6, further comprising a fourth panel connected to said second panel at a third fold line along said distal side of said second panel.

8. The suture package of claim 7, wherein said fourth panel has a third slit sized and shaped to form a locking tab; and said first panel has a third slot sized and shaped to receive said locking tab.

9. The suture package of claim 8, further comprising a first end panel attached to one end of said first panel along a fourth fold line; a second end panel attached to an opposite end of said first panel along a fifth fold line; a third end panel attached to one end of said second panel along a sixth fold line; and a fourth end panel attached to an opposite end of said second panel along a seventh fold line.

10. The suture package of claim 9, wherein said third end panel has a first tab and said fourth end panel has a second tab; said first end panel has a first slit sized and shaped to receive said first tab along said fourth fold line; and said second end panel has a second slit sized and shaped to receive said second tab along said fifth fold line.

11. The suture package of claim 10, wherein said first end panel overlaps said third end panel, said first end panel and said third end panel cooperate to maintain the pillow-shape of said envelope; and said second end panel overlaps said fourth end panel, said second end panel and said fourth end panel cooperate to maintain the pillow-shape of said envelope.

12. The suture package of claim 11, further comprising a plurality of holes located proximate to said first fold line and sized and shaped to allow pins of a suture winding apparatus to pass thereth rough.

13. The suture package of claim 8, further comprising a first end panel attached to one end of said first panel along a fourth fold line; a second end panel attached to an opposite end of said first panel along a fifth fold line; a first flap attached to said first end panel along a sixth fold line; and a second flap attached to said second end panel along a seventh fold line.

14. The suture package of claim 13, wherein said first end panel is substantially perpendicular to said first panel after said first flap is folded about said sixth fold line; and said second end panel is substantially perpendicular to said first panel after said second flap is folded about said seventh fold line.

15. The suture package of claim 14, further comprising a plurality of holes located in said first panel.

16. A suture package, comprising a first panel, said first panel bulging outwardly in a first direction so as to assume a first arcuate shape; a second panel connected to said first panel at a first fold line along one side of said first panel, said second panel bulging outwardly in a second direction substantially opposite to said first direction so as to assume a second arcuate shape; a third panel connected to said first panel at a second fold line along an opposite side of said first panel, said first panel and said second panel being foldable relative to each other along said first fold line to form an envelope having an interior hollow, said third panel extending within said envelope and having a width which is substantially smaller than the width of said first panel; and a suture positioned within said interior hollow between said second panel and said third panel, said third panel bulging outwardly in said second direction such that said third panel assumes a third arcuate shape which substantially matches said second arcuate shape of said second panel and such that said third panel is biased toward said second panel so as to urge a said suture against said second panel.

17. The suture package of claim 16, wherein said suture package is made from a blank, which includes first, second, and third panels.

* * * * *

UNITED STATES PATENT AND TRADEMARK OFFICE
CERTIFICATE OF CORRECTION

| | | |
|---|---|---|
| PATENT NO. | : 6,719,128 B2 | Page 1 of 1 |
| DATED | : April 13, 2004 | |
| INVENTOR(S) | : Marvin Alpern and Delfin A. Lorenzo Iglesias | |

It is certified that error appears in the above-identified patent and that said Letters Patent is hereby corrected as shown below:

<u>Column 7,</u>
Line 15, please delete "thereth rough" and insert therefore -- therethrough --

Signed and Sealed this

Seventeenth Day of August, 2004

JON W. DUDAS
*Acting Director of the United States Patent and Trademark Office*